United States Patent [19]

Kusaba et al.

[11] Patent Number: 4,933,366
[45] Date of Patent: Jun. 12, 1990

[54] FUNGICIDAL COMPOSITION

[75] Inventors: Tomoyuki Kusaba, Toyonaka; Junya Takahashi, Hyogo; Masayo Sugano, Osaka; Tamon Uematsu, Kobe; Yukio Oguri, Toyonaka; Tomohiro Teramae, Takarazuka, all of Japan

[73] Assignee: Sumitomo Chemical Company, Limited, Osaka, Japan

[21] Appl. No.: 370,094

[22] Filed: Jun. 22, 1989

Related U.S. Application Data

[63] Continuation of Ser. No. 84,884, Aug. 13, 1987, abandoned.

[30] Foreign Application Priority Data

Aug. 26, 1986 [JP] Japan .................. 61-200274
Aug. 26, 1986 [JP] Japan .................. 61-200275
Aug. 26, 1986 [JP] Japan .................. 61-200276
Dec. 22, 1986 [JP] Japan .................. 61-307390
Dec. 23, 1986 [JP] Japan .................. 61-315812

[51] Int. Cl.$^5$ .............................. A01N 47/70
[52] U.S. Cl. ........................ 514/485; 560/30; 560/33
[58] Field of Search ............ 514/485; 560/30, 33

[56] References Cited

U.S. PATENT DOCUMENTS 3,923,870 12/1975 Singer .................. 560/24

FOREIGN PATENT DOCUMENTS 40-3903  2/1965 Japan .
230119 10/1969 U.S.S.R. .
2138292 10/1984 United Kingdom .
2140299 11/1984 United Kingdom .

OTHER PUBLICATIONS

Khim. Farm. Zh., 19, No. 12, 1445-1456 (1985) w/Abstract (PESTDOC, 86-84488).
Chem. Abstracts, 96, 173935u (1982).

Primary Examiner—Bruce Gray
Attorney, Agent, or Firm—Stevens, Davis, Miller & Mosher

[57] ABSTRACT

A fungicidal composition which comprises as an active ingredient a fungicidally effective amount of the compound represented by the general formula,

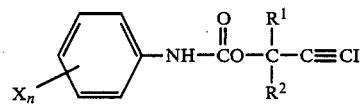

wherein X, which may be the same or different, represents a hydrogen or halogen atom or a lower alkyl group, $R^1$ and $R^2$, which may be the same or different, represent a hydrogen atom or a methyl group, and n represents an integer of from 1 to 5, and an inert carrier.

1 Claim, No Drawings

FUNGICIDAL COMPOSITION

This application is a continuation of application Ser. No. 07/084,884, filed Aug. 13, 1987 now abandoned.

The present invention relates to agricultural and horticultural fungicides containing an iodopropargyl N-phenylcarbamate as an active ingredient.

Hitherto, dithiocarbamate compounds such as Mancozeb, Maneb, etc. and phthalimide compounds such as Captan, Difolatan, etc. are well known as an agricultural and horticultural fungicide having a wide antimicrobial activity.

Japanese Patent Publication Kokai (Laid-open) No. 193860/1984, etc. disclose that some of the compounds described in the present invention have activity against algae, but nothing is described about their agricultural and horticultural fungicidal activity.

However, agricultural and horticultural fungicides such as Mancozeb, Maneb, Captan, Difolatan, etc., in spite of their wide antimicrobial activity, may not always be said to have a practical controlling effect against all diseases, and also unless they are used in large amounts such as 1 to 2 kg/ha as an active ingredient, a sufficient effect cannot be expected. Said fungicides, therefore, were not always satisfactory as an agricultural and horticultural fungicide.

In view of the situation like this the present inventors extensively studied to develop excellent agricultural and horticultural fungicides, and as a result, found that the iodopropargyl N-phenylcarbamate of the present invention is a compound having few problems described above and excellent fungicidal activity. The present inventors thus attained to the present invention.

The present invention provides a fungicidal composition for agricultural and horticultural purposes characterized by containing as an active ingredient a carbamate derivative represented by the general formula

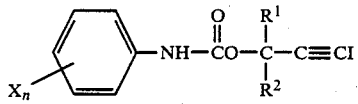
(I)

wherein X which may be the same or different, represents a hydrogen or halogen atom or a lower alkyl group, $R^1$ and $R^2$, which may be the same or different, a hydrogen atom or a methyl group, and n represents an integer of from 1 to 5.

The present invention will be explained in more detail.

The carbamate derivative represented by the general formula (I) can be produced, for example, by reacting a phenyl isocyanate derivative represented by the general formula,

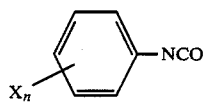

wherein X, which may be the same or different, represents a hydrogen or halogen atom or a lower alkyl group, and n represents an integer of from 1 to 5, with an iodopropargyl alcohol derivative. This reaction can be carried out at a temperature of from room temperature to 100° C in from a moment to 12 hours in a solvent. This solvent includes for example aromatic hydrocarbons (e.g. toluene, benzene), ethers [e.g. diethyl ether, tetrahydrofuran (THF)], halogenated hydrocarbon (e.g. chloroform, dichloromethane), etc.

Also, tertiary amines such as pyridine, triethylamine, etc. may be used as a reaction catalyst.

For plant diseases which can be controlled with the present compounds, there are given downy mildew of vegetables and Japanese radish (*Peronospora brassicae*), downy mildew of spinach (*Peronospora spinaciae*), downy mildew of tobacco (*Peronospora tabacina*), downy mildew of cucumber (*Pseudoperonospora cubensis*), downy mildew of grape (*Plasmopara viticola*), downy mildew of dropwort (*Plasmopara nivea*), late blight of apple, strawberry and ginseng (*Phytophthora cactorum*), phytophthora rot of tomato and cucumber (*Phytophthora capsici*), late blight of pineapple (*Phytophthora cinnamomi*), late blight of potato, tomato and eggplant (*Phytophthora infestans*), late blight of tobacco, broad bean and Welsh onion (*Phytophthora nicotianae var. nicotianae*), damping-off of spinach (*Pythium sp.*) damping-off of cucumber (*Pythium aphanidermatum*), browning root rot of wheat (*Pythium sp.*), damping-off of tobacco (*Phythium debaryanum*) pythium rot of soybean (*Pythium aphanidermatum, P. debaryanum, P. irregulare, P. myriotylum, P. ultimam*), blast of rice (*Pyricularia oryzae*), brown spot of rice (*Cochliobolus miyabeanus*), scab of apple (*Venturia inaequalis*), canker of apple (*Valsa mali*), alternaria leaf spot of apple (*Alternaria mali*), black spot of pear (*Alternaria kikuchiana*), scab of pear (*Venturia nashicola*), melanose of citrus (*Diaporthe citri*), common green mold of citrus (*Penicillium digitatum*), blue mold of citrus (*Penicillium italicum*), phomopsis rot of peach (*Phomopsis sp.*), anthracnose of Japanese persimmon (*Gloeosporium kaki*), leaf spot of Japanese persimmon (*Cercospora kaki, Mycosphaerella nawae*), ripe rot of grape (*Glomerella cingulata*), gray mold of grape (*Botrytis cinerea*), stripe of barley (*Helminthosporium gramineum*), loose smut of barley (*Ustilago nuda*), speckled leaf blotch of wheat (*Septoria tritici*), glume blotch of wheat (*Leptosphaeria nodorum*), eye spot of wheat (*Pseudocercosporella herpotrichoides*), powdery mildew of wheat and barley (*Erysiphe graminis*), rust of wheat and barley (*Puccinia graminis, P. striiformis, P. recondita*), anthracnose of melons (*Colletotrichum lagenarium*), gummy stem blight of melons (*Mycosphaerella melonis*), powdery mildew of melons (*Sphaerotheca fuliginea*), early blight of tomato (*Alternaria solani*), brown spot of tobacco (*Alternaria longipes*) anthracnose of tobacco (*Colletotrichum tabacum*), cercospora leaf spot of beet (*Cercospora beticola*), early blight of potato (*Alternaria solani*), brown leaf spot of peanut (*Cercospora arachidicola*), septoria brown spot of soybean (*Septoria qlycines*), melanose of soybean (*Diaporthe phaseololum*), anthracnose of soybean (*Colletotrichum sp.*), purple stain of soybean (*Cercospora kikuchii*), etc.

From the standpoint of fungicidal activity, the agricultural and horticultural fungicides of the present invention are more preferably the followings:

3-Iodopropargyl N-phenylcarbamate
3-Iodopropargyl N-(4-chlorophenyl)carbamate
3-Iodopropargyl N-(3,4-dichlorophenyl)carbamate
3-Iodopropargyl N-(2-chlorophenyl)carbamate
3-Iodopropargyl N-(2-fluorophenyl)carbamate and
1-Methyl-3-iodopropargyl N-phenylcarbamate.

For the agricultural and horticultural fungicides of the present invention, only the present compounds, which are an active ingredient, may be used. Generally, however, they are formulated before use into emulsifiable concentrates, wettable powders, suspension formulations, dusts, liquid formulations, etc. by mixing with solid carriers, liquid carriers, surface active agents and other auxiliaries for formulation. In this case, the content of the present compounds, which are an active ingredient, in these preparations is from 0.1 to 99.9%, preferably from 1 to 90%.

The solids carriers include fine powders or granules of kaolin clay, attapulgite clay, bentonite, terra abla, pyrophyllite, talc, diatomaceous earth, calcite, corn stalk powder, walnut shell powder, urea, ammonium sulfate, synthetic hydrated silicon dioxide, etc. The liquid carriers include aromatic hydrocarbons (e.g. xylene, methylnaphthalene), alcohols (e.g. isopropanol, ethylene glycol, cellosolve), ketones (e.g. acetone, cyclohexanone, isophorone), vegetable oils (e.g. soybean oil, cotton seed oil), dimethyl sulfoxide, acetonitrile, water, etc. The surface active agents used for emulsification, dispersion, wetting, etc. include anionic surface active agents such as the salt of alkyl sulfates, alkyl-(aryl)sulfonates, dialkyl sulfosuccinates, the salt of polyoxyethylene alkylaryl ether phosphoric acid esters, naphthalenesulfonic acid/formalin condensates, etc. and nonionic surface active agents such as polyoxyethylene alkyl ether, polyoxyethylene polyoxypropylene block copolymers, sorbitan fatty acid esters, polyoxyethylene sorbitan fatty acid esters, etc. The auxiliaries for formulation include lignosulfonates, alginates, polyvinyl alcohol, gum arabic, CMC (carboxymethyl cellulose), PAP (isopropyl acid phosphate), etc.

A method for applying the agricultural and horticultural fungicides of the present invention includes for example foliar application, soil treatment, seed disinfection, etc., but any of the methods generally used by those skilled in the art exhibit a sufficient effect. The dosage rate of he active ingredient of the agricultural and horticultural fungicides of the present invention varies with crops and diseases aimed at, degree of outbreak of diseases, preparation forms, application methods, application time, weather conditions, etc., but it is generally from 0.5 to 200 g/are, preferably from 1 to 100 g/are. When the emulsifiable concentrates, wettable powders, suspension formulations, liquid formulations, etc. are applied in dilution with water, the application concentration of the present compounds is from 0.005 to 0.5%, preferably from 0.01 to 0.2%. The dusts, granules, etc. are applied as they are without dilution.

Further, the agricultural and horticultural fungicides of the present invention can be used for plow fields, paddy fields, orchards, tea gardens, pastures, turfs, etc., and also an increase in the fungicidal activity can be expected by using them in mixture with other plant disease-controlling agents. In addition, they can be used in mixture with insecticides, acaricides, nematocides, herbicides, plant growth regulators, fertilizers, etc.

The present invention will be illustrated in more detail with reference to the following production example, formulation examples and test examples.

PRODUCTION EXAMPLE

To 30 ml of a dry tetrahydrofuran solution containing 1.8 g (10 mmoles) of 3-iodopropargyl alcohol and one drop of triethylamine was added 1.2 g (10 mmoles) of phenyl isocyanate, followed by stirring at room temperature for 12 hours. The solvent was removed by vaporization under reduced pressure, and the residue was recrystallized from ethyl acetate to obtain 1.5 g of 3-iodopropargyl N-phenylcarbamate.

m.p., 145–146° C.

Some of the present compounds which can be produced by this method will be shown in Table 1.

TABLE 1

Carbamate derivative represented by the general formula:

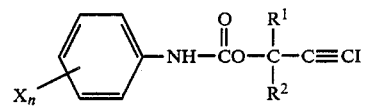

| Compound No. | $X_n$ | $R^1$ | $R^2$ | Physical constant |
|---|---|---|---|---|
| 1 | (phenyl) | H | H | mp, 145–146° C. |
| 2 | 2-CH₃-phenyl | H | H | $n_D^{20}$ 1.5888 |
| 3 | 2-Cl-phenyl | H | H | mp, 84–85° C. |
| 4 | 4-Cl-phenyl | H | H | mp, 106–107° C. |
| 5 | 2,4-diCl-phenyl | H | H | |
| 6 | 2,6-diCl-phenyl | H | H | mp, 93–94° C. |
| 7 | 2,4-diCl-phenyl | H | H | mp, 115–116° C. |
| 8 | 4-CH₃-phenyl | H | H | $n_D^{20}$ 1.5888 |

TABLE 1-continued

Carbamate derivative represented by the general formula:

$$X_n-\text{C}_6\text{H}_4-\text{NH}-\overset{\overset{\text{O}}{\|}}{\text{CO}}-\overset{\overset{R^1}{|}}{\underset{\underset{R^2}{|}}{\text{C}}}-\text{C}\equiv\text{CI}$$

| Compound No. | $X_n$ (phenyl substituent) | $R^1$ | $R^2$ | Physical constant |
|---|---|---|---|---|
| 9 | 2-CH₃-phenyl | H | H | mp, 80–81° C. |
| 10 | 2-Cl-phenyl | H | H | mp, 88–89° C. |
| 11 | 2-F-phenyl | H | H | mp, 91–92° C. |
| 12 | 4-F-phenyl | H | H | mp, 169–170° C. |
| 13 | pentafluorophenyl (2,3,4,5,6-F₅) | H | H | mp, 116–117° C. |
| 14 | 4-iso-C₃H₇-phenyl | H | H | mp, 104–105° C. |
| 15 | 3-C₂H₅-phenyl | H | H | $n_D^{20}$ 1.5448 |
| 16 | 3,5-(CH₃)₂-phenyl | H | H | mp, 95–96° C. |
| 17 | phenyl | H | CH₃ | mp, 139–140° C. |
| 18 | 2,3-diCl-phenyl | H | CH₃ | Highly viscous liquid |
| 19 | 3-CH₃-phenyl | H | CH₃ | $n_D^{19}$ 1.5781 |
| 20 | 4-CH₃-phenyl | H | CH₃ | mp, 90–91° C. |
| 21 | 3-Cl-phenyl | H | CH₃ | $n_D^{21.5}$ 1.5791 |
| 22 | 4-Cl-phenyl | H | CH₃ | $n_D^{21.5}$ 1.5781 |

Formulation examples will be shown. In the examples, all parts are by weight.

FORMULATION EXAMPLE 1

Fifty parts of each of the present compounds (1) to (22), 3 parts of calcium lignosulfonate, 2 parts of sodium lauryl sulfate and 45 parts of synthetic hydrated silicon dioxide are well pulverized and mixed to obtain a wettable powder of each compound.

FORMULATION EXAMPLE 2

Twenty-five parts of each of the present compounds (1) to (22), 3 parts of polyoxyethylene sorbitan monooleate, 3 parts of CMC and 69 parts of water are mixed and wet-pulverized until the particle size of the active ingredient is reduced to 5 microns or less to obtain a suspension formulation of each compound.

FORMULATION EXAMPLE 3

Two parts of each of the present compounds (1) to (22), 88 parts of kaolin clay and 10 parts of talc are well pulverized and mixed to obtain a dust of each compound.

FORMULATION EXAMPLE 4

Twenty parts of each of the present compounds (1) to (22), 14 parts of polyoxyethylene styrylphenyl ether, 6 parts of calcium dodecylbenzenesulfonate and 60 parts of xylene are well mixed to obtain an emulsifiable concentrate of each compound.

FORMULATION EXAMPLE 5

Two parts of each of the present compounds (1) to (22), 1 part of synthetic hydrated silicon dioxide, 2 parts of calcium lignosulfonate, 30 parts of bentonite and 65 parts of kaolin clay are well pulverized and mixed, well kneaded with water, granulated and dried to obtain a granule of each compound. Test examples for the agricultural and horticultural fungicides of the present invention will be shown. Test compounds are shown by Compound No. in Table 1, and compounds used as a control are shown by Compound symbol in Table 2.

TABLE 2

| Compound symbol | Structural formula | Remark |
| --- | --- | --- |
| A | $CuSO_4 \cdot XCu(OH)_2 \cdot YCa(OH)_2 \cdot ZH_2O$ | Commercial product (copper wettable powder) |
| B | 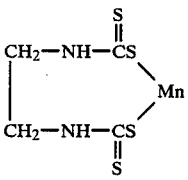 | Commercial product (Maneb) |

The controlling activity was expressed in six stages described below, 5, 4, 3, 2, 1, 0, according to the condition of disease of test plants at the time of examination, i.e. the degree of colony and infected area on the leaves, stems, etc., observed with the naked eyes.

5 Neither colony nor infected area is observed.
4 About 10% of colony or infected area is observed.
3 About 30% of colony or infected area is observed.
2 About 50% of colony or infected area is observed.
1 About 70% of colony or infected area is observed
0 More than about 70% of colony or infected area is observed, there being no difference in the condition of disease between the treated and untreated plots.

TEST EXAMPLE 1

Controlling test on late blight of potato (*Phytophthora infestans*) (preventive effect)

Sandy loam was filled in plastic pots, and potato (var., Danshaku) was sowed and cultivated into seedlings for 20 days in a greenhouse. The wettable powder of each test compound prepared according to Formulation example 1 was diluted with water to a prescribed concentration and foliar-sprayed onto the seedlings so that the spray liquor was thoroughly attached to the leaf surface. After spraying, the seedlings were inoculated by spraying the spore suspension of *Phytophthora infestans*. After inoculatin, the seedlings were cultivated firstly at 20° C. for 1 day under a highly humid condition, and then under lighting for 5 days to examine the controlling activity. The results are shown in Table 3.

TABLE 3

| Test compound | | Controlling activity |
| --- | --- | --- |
| Compound No. | Application concentration of active ingredient (ppm) | |
| 1 | 200 | 5 |

TABLE 3-continued

| Test compound | | Controlling activity |
| --- | --- | --- |
| Compound No. | Application concentration of active ingredient (ppm) | |
| 2 | 200 | 5 |
| 3 | 200 | 5 |
| 4 | 200 | 5 |
| 5 | 200 | 5 |
| 6 | 200 | 5 |
| 7 | 200 | 5 |
| 8 | 200 | 5 |
| 9 | 200 | 5 |
| 10 | 200 | 5 |
| 11 | 200 | 5 |
| 13 | 200 | 5 |
| 14 | 200 | 5 |
| 16 | 200 | 5 |
| 17 | 200 | 5 |
| 18 | 200 | 5 |
| 20 | 200 | 5 |
| 22 | 200 | 5 |
| A | 200 | 3 |
| B | 200 | 4 |

TEST EXAMPLE 2

Controlling test on downy mildew of grape (*Plasmopara viticola*) (preventive effect)

Sandy loam was filled in plastic pots, and grape was sowed and cultivated into seedlings in the 5th to 6th true leaf stage for 50 days in a greenhouse. The wettable powder of each test compound prepared according to Formulation example 1 was diluted with water to a prescribed concentration and foliar-sprayed onto the seedlings so that the spray liquor was thoroughly attached to the leaf surface. After spraying, the seedlings were inoculated by spraying the spore suspension of *Plasmopara viticola*. After inoculation, the seedlings were cultivated firstly at 20° C for 1 day under a highly humid condition and then under lighting for 8 days to examine the controlling activity. The results are shown in Table 4.

TABLE 4

| Test compound | | Controlling activity |
| --- | --- | --- |
| Compound No. | Application concentration of active ingredient (ppm) | |
| 1 | 200 | 5 |
| 2 | 200 | 5 |
| 3 | 200 | 5 |
| 4 | 200 | 5 |
| 7 | 200 | 5 |
| 14 | 200 | 5 |
| 16 | 200 | 5 |
| 17 | 200 | 5 |
| A | 200 | 2 |

TEST EXAMPLE 3

Controlling test on eye spot of wheat (*Pseudocercosporella herpotrichoides*) (preventive effect)

Sandy loam was filled in plastic pots, and wheat (var., Norin No. 73) was sowed and cultivated into seedlings for 10 days in a greenhouse. The wettable powder of each test compound prepared according to Formulation example 1 was diluted with water to a prescribed concentration and foliar-sprayed onto the seedlings so that the spray liquor was thoroughly attached to the leaf surface. After spraying, the seedlings were air-dried and inoculated by spraying the spore suspension of *Pseudocercosporella herpotrichoides*. After inoculation, the seedlings were cultivated firstly at 15° C. in the dark under a highly humid condition for 4 days and then under lighting and a highly humid condition for 4 days to examine the controlling activity. The results are shown in Table 5.

TABLE 5

| Test compound | | |
|---|---|---|
| Compound No. | Application concentration of active ingredient (ppm) | Controlling activity |
| 1 | 500 | 4 |
| 3 | 500 | 4 |
| 4 | 500 | 3 |
| 5 | 500 | 3 |
| 9 | 500 | 5 |
| 11 | 500 | 5 |
| 17 | 500 | 4 |
| 18 | 500 | 5 |
| 22 | 500 | 4 |
| A | 500 | 1 |

TEST EXAMPLE 4

Controlling test on scab of apple (*Venturia inaequalis*) (preventive effect)

Sandy loam was filled in plastic pots, and apple was sowed and cultivated into seedlings in the 4th to 5th true leaf stage for 20 days in a greenhouse. The wettable powder of each test compound prepared according to Formulation example 1 was diluted with water to a prescribed concentration and foliar-sprayed onto the seedlings so that the spray liquor was thoroughly attached to the leaf surface. After spraying, the seedlings were inoculated by spraying the spore suspension of *Venturia inaequalis*. After inoculation, the seedlings were cultivated firstly at 1520 C. under a highly humid condition for 4 days and then under lighting for 15 days to examine the controlling activity. The results are shown in Table 6.

TABLE 6

| Test Compound | | |
|---|---|---|
| Compound No. | Application concentration of active ingredient (ppm) | Controlling activity |
| 1 | 200 | 5 |
| 2 | 200 | 5 |
| 3 | 200 | 5 |
| 4 | 200 | 5 |
| 5 | 200 | 5 |
| 7 | 200 | 4 |
| 9 | 200 | 4 |
| 10 | 200 | 4 |
| 11 | 200 | 5 |
| 13 | 200 | 5 |
| 17 | 200 | 5 |
| 20 | 200 | 5 |
| 22 | 200 | 4 |

TABLE 6-continued

| Test Compound | | |
|---|---|---|
| Compound No. | Application concentration of active ingredient (ppm) | Controlling activity |
| A | 200 | 3 |

TEST EXAMPLE 5

Controlling test on speckled leaf blotch of wheat (*Septoria tritici*) (preventive effect)

Sandy loam was filled in plastic pots, and wheat (var., Norin No. 73) was sowed and cultivated into seedlings for 8 days in a greenhouse. The wettable powder of each test compound prepared according to Formulation example 1 was diluted with water to a prescribed concentration and foliar-sprayed onto the seedlings so that the spray liquor was thoroughly attached to the leaf surface. After spraying, the seedlings were inoculated by spraying the spore suspension of *Septoria tritici*. After inoculation, the seedlings were cultivated firstly at 15° C. in the dark under a highly humid condition for 3 days and then at 15° C. under lighting for 15 days to examine the controlling activity. The results are shown in Table 7.

TABLE 7

| Test compound | | |
|---|---|---|
| Compound No. | Application concentration of active ingredient (ppm) | Controlling activity |
| 1 | 500 | 5 |
| 2 | 500 | 5 |
| 3 | 500 | 5 |
| 4 | 500 | 5 |
| 6 | 500 | 5 |
| 12 | 500 | 5 |
| 14 | 500 | 5 |
| 19 | 500 | 5 |
| 20 | 500 | 5 |
| 21 | 500 | 4 |
| B | 500 | 3 |

What is claimed is:

1. A method for controlling plant pathogenic fungi which comprises applying a fungicidally effective amount of the compound represented by the general formula,

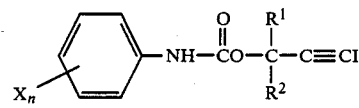

wherein X, which may be the same or different, represents a hydrogen or halogen atom or a lower alkyl group, $R^1$ and $R^2$, which may be the same or different represent a hydrogen atom or a methyl group, and n represents an integer of from 1 to 5, to plant pathogenic fungi.

* * * * *